United States Patent [19]

Lynch

[11] 4,196,140
[45] Apr. 1, 1980

[54] RECOVERY OF WASTE STREAMS CONTAINING RECOVERABLE CHLORINE

[75] Inventor: Richard W. Lynch, Chattanooga, Tenn.

[73] Assignee: Olin Corporation, New Haven, Conn.

[21] Appl. No.: 946,691

[22] Filed: Sep. 28, 1978

[51] Int. Cl.$^2$ ............................................. C07C 71/00
[52] U.S. Cl. ................................ 260/453 R; 423/164; 423/197
[58] Field of Search ............... 423/473, 474, 499, 164, 423/197; 260/453 R

[56] References Cited

U.S. PATENT DOCUMENTS

| 1,632,483 | 6/1927 | MacMullan | 423/474 |
| 2,694,722 | 11/1954 | Katz | 260/453 R X |
| 3,954,948 | 5/1976 | Sakowski | 423/473 |

OTHER PUBLICATIONS

Chattaway et al. "Alkyl Hypochlorites" *Journal Chemical Society* vol. 123 (1923) pp. 2999-3003.
Fort et. al. "Alkyl Hypochlorites" as abstracted in *Chemical Abstracts* vol. 49 (1955) # 12,271a.
Jolly, "The Synthesis and Characterization of Inorganic Compounds" Prentice-Hall, Inc., New Jersey, 1970, pp.97, 99-101.

*Primary Examiner*—O. R. Vertiz
*Assistant Examiner*—Thomas W. Roy
*Attorney, Agent, or Firm*—Gordon F. Sieckmann; Donald F. Clements

[57] ABSTRACT

A process is disclosed for recovering recoverable chlorine from chemical plant waste streams.

An aqueous stream containing recoverable chlorine is reacted with an alkali metal hydroxide, such as sodium hydroxide, to form a slurry of solid particles of alkaline earth metal hydroxide, such as calcium hydroxide, suspended in a liquid. The calcium hydroxide is filtered or otherwise separated from the liquid. The liquid is admixed with an organic alcohol to form an organic-aqueous solution. A halogenating agent, such as chlorine, is reacted with the organic-aqueous solution to form a solution of organic hypochlorite in an organic phase and an aqueous phase.

The solution of organic hypochlorite is phase separated to form aqueous and organic phases. The aqueous phase containing sodium chloride may be recycled for use as a reactant in a chlor-alkali electrolytic cell.

The organic phase containing organic hypochlorite may be used as a chlorinating agent or may be treated with an acid, such as hydrochloric acid, to reclaim free chlorine.

34 Claims, No Drawings

RECOVERY OF WASTE STREAMS CONTAINING RECOVERABLE CHLORINE

This invention is a process for recovering recoverable chlorine from aqueous waste streams as an organic hypohalite and an alkali metal halide.

Several chemical and electrochemical processes for preparing organic hypohalites are taught by the prior art.

For example, U.S. Pat. No. 1,938,175, issued Dec. 5, 1933, to Richard M. Deanesly, discloses a chemical process for preparing alkyl hypochlorites according to the following equations:

(1)

(2)

where ROH is any aliphatic alcohol of primary, secondary, or tertiary character and ROCl is the organic hypochlorite corresponding to that organic alcohol.

In *Encyclopedia of Chemical Technology*, by Kirk-Othmer, 2nd Edition, Volume 5, pages 24–25, a variety of chemical processes are employed for preparing organic hypohalites. Reference is made to solutions prepared with carbon tetrachloride, chloroform, or o-dichlorobenzene.

In another example, U.S. Pat. No. 3,449,225, issued to Edwin A. Matzner on June 10, 1969, an electrolytic process is disclosed for preparing organic hypohalites from inorganic halides and organic compounds.

There is a long felt need at the present time for a low energy economical process for purifying waste streams containing high concentrations of recoverable chlorine so that such streams thereafter may suitably contact activated carbon beds in municipal effluent treatment plants.

There is also a long felt need at the present time to operate plants which produce recoverable chlorine compounds by maximizing recycle and minimizing discharge of aqueous chemical plant waste streams in view of the strong environmental protection position of federal and state governments.

There is a long felt need for an economical process of recovering recoverable chlorine in the waste streams of chemical plants which produce alkali metal halides, alkaline earth hypohalites and the like.

OBJECTS

It is a primary object of the invention to provide a process for economically recovering recoverable chlorine content of waste streams formed in chemical plants which produce alkali metal halides, alkaline earth metal hypohalites, and the like.

It is a further object of the invention to provide a process for modifying waste streams formed in plants used in the production of calcium hypochlorite in order to permit contact between these purified streams and activated carbon beds employed in water purification systems.

An additional object of the invention is to provide a low energy process for treating recoverable chlorine from waste streams produced in calcium hypochlorite plants, thereby minimizing the amount of raw material usage.

These and other objects of the invention will be apparent from the following detailed description and the appended claims.

BRIEF DESCRIPTION OF THE INVENTION

It has now been discovered that the foregoing objects are accomplished in a process for recovering recoverable chlorine from aqueous waste streams which comprises reacting impure aqueous solution containing recoverable chlorine with an alkali metal hydroxide, such as sodium hydroxide, to form a slurry of solid particles of alkaline earth metal hydroxide, such as calcium hydroxide, suspended in a liquid. The calcium hydroxide particles are separated from the liquid and the liquid is admixed with an organic alcohol. A halogenating agent, such as chlorine, is reacted with the resulting organic-aqueous solution to form an aqueous phase and an organic phase containing organic hypochlorite. The organic phase containing organic hypochlorite is phase separated from the aqueous phase.

DETAILED DESCRIPTION OF THE INVENTION

A typical aqueous waste stream containing recoverable chlorine which may be treated according to the process of this invention is one that is produced as a plant effluent in chemical plants used in the preparation of calcium hypochlorite. The process of this invention will be described as it is applied to the purification of such effluent. However, those skilled in the art will recognize that the same treatment may be applied to other recoverable chlorine waste streams of the type produced in alkali metal hypochlorite plants such as sodium hypochlorite plants, other alkaline earth metal hypochlorites, and the like.

As indicated in *Encyclopedia of Chemical Technology*, by Kirk-Othmer, 2nd Edition, Volume 5, pages 16–25, a variety of chemical processes are employed for preparing calcium hypochlorite. Each plant effluent from these processes will have a different detailed analysis, depending upon the reaction used in the preparation of calcium hypochlorite, the efficiency of the process, and the plant operation. However, each will have an excess of available chlorine in the form of calcium hypochlorite, sodium hypochlorite or mixture thereof. A typical analysis of such an effluent from a typical calcium hypochlorite plant is illustrated as follows:

| Component | Typical Analysis | Min./Max. Analysis |
| --- | --- | --- |
| Ca(OCl)$_2$ | 18 grams per liter | 4 to 80 gpl |
| NaCl | 60 grams per liter | 25 to 200 gpl |
| Ca(OH)$_2$ | 2 grams per liter | <1 to 10 gpl |
| Ca(ClO$_3$)$_2$ | 3 grams per liter | 1 to 15 gpl |
| CaCl$_2$ | 35 grams per liter | <1 to 200 gpl |

Because of the solubility characteristics of calcium hypochlorite and the size of occasional spills occurring during processing, it is extremely difficult to economically remove all the calcium hypochlorite in the plant process streams prior to reaching the waste stream effluent. As a result, the chemical analyses of the waste effluent may vary from the ranges indicated above.

In the first reaction step of the process of this invention, an impure aqueous solution of the type described previously, containing recoverable chlorine, is reacted with an aqueous solution of an alkali metal hydroxide.

The term "recoverable chlorine" includes (i) alkaline earth metal halides such as calcium chloride, calcium bromide, and mixtures thereof, (ii) alkaline earth metal hypohalites such as calcium hypochlorites, calcium hypobromites, and mixtures thereof, (ii) alkaline earth metal chlorates such as calcium chlorate, (iv) alkali metal hypohalites such as sodium hypochlorite, sodium hypobromite, and mixtures thereof, and (iv) mixtures of alkaline earth metal halides, alkaline earth metal hypohalites, alkaline earth metal chlorates, and alkali metal hypohalites mentioned above.

Additionally, one skilled in the art will recognize that the presence in the impure aqueous stream of an alkali metal halide such as sodium chloride, and an alkali metal chlorate such as sodium chlorate, are not strict requirements of this invention, but will recognize that alkali metal halides and alkali metal chlorates are expected components in the impure waste streams of a typical chemical plant producing alkali metal hypochlorites, alkaline earth metal hypochlorites, and the like.

In the first reaction step of the process of this invention, the impure aqueous solution is reacted with an alkali metal hydroxide. Suitable alkali metal hydroxides include potassium hydroxides, sodium hydroxides, lithium hydroxides, and mixtures thereof, having a concentration in the range from about 5% to about 55% alkali metal hydroxide by weight, and preferably from about 7% to about 50% alkali metal hydroxide by weight.

Since aqueous solutions of alkali metal hydroxides, such as sodium hydroxide, may be produced in chemical plants producing alkali metal hypochlorites and alkaline earth metal hypochlorites, the process of this invention employs a reactant which is readily available in plants which produce the waste streams to be treated.

One skilled in the art will recognize that any suitable technique for the preparation of aqueous alkali metal hydroxide solutions will suffice for the purpose of this invention.

The first reaction step is represented by equations (3)-(5). Recoverable chlorine present in the impure aqueous stream, for example, as an alkaline earth metal hypohalite such as calcium hypochlorite reacts with the alkali metal hydroxide such as sodium hydroxide, to form sodium hypochlorite and a solid alkaline earth metal hydroxide such as calcium hydroxide according to the equation (3):

$$Ca(OCl)_2 + 2NaOH \rightarrow 2NaOCl + Ca(OH)_2. \quad (3)$$

Recoverable chlorine present in the impure aqueous stream, for example, as an alkaline earth metal halide such as calcium chloride reacts with sodium hydroxide to form sodium chloride and solid alkaline earth metal hydroxide such as calcium hydroxide according to the equation (4):

$$CaCl_2 + 2NaOH \rightarrow 2NaCl + Ca(OH)_2. \quad (4)$$

Recoverable chlorine present in the impure aqueous stream, for example, as an alkaline earth metal chlorate such as calcium chlorate reacts with sodium hydroxide to form sodium chlorate and calcium hydroxide according to the equation (5):

$$Ca(ClO_3)_2 + 2NaOH \rightarrow 2NaClO_3 + Ca(OH)_2. \quad (5)$$

As can be seen from equations (3)-(5), the molar ratio of the alkali metal hydroxide such as sodium hydroxide, for each mole of alkaline earth metal species, such as alkaline earth metal halide, alkaline earth metal hypohalite, and alkaline earth metal chlorate, is in the range from about 1.5:1 to about 3:1, and preferably from about 2:1 to about 2.5:1 to complete conversion of all alkaline earth metal species, which is essentially stoichiometric.

The temperature of the reaction zone described in equations (3)-(5) is in the range from about 20° C. to about 50° C., and preferably from about 25° C. to about 40° C.

The reaction time required for the reactions described in equations (3)-(5) is in the range from about 5 to about 60 minutes, and preferably from about 10 to about 40 minutes.

Completion of the reactions in equations (3)-(5) result in the formation of a slurry of solid particles of alkaline earth metal hydroxide, such as calcium hydroxide, suspended in a liquid.

The liquid is comprised of sodium hypochlorite, sodium chloride, sodium chlorate, sodium hydroxide, and water.

The solid calcium hydroxide particles are separated from the liquid by any suitable solid-liquid separation technique, such as by filtration, centrifuging, settling, and the like. Filtration is the preferred form of solid-liquid separation. One skilled in the art will recognize that any other suitable solid-liquid separation technique may be employed.

The solid calcium hydroxide particles separated from the liquid solution contain a minimal amount of residual liquid and may be disposed of as waste or otherwise utilized.

The liquid is admixed with an organic alcohol and an organic solvent, if desired, to form an organic-aqueous solution.

The time required for adequate mixing of the liquid with the organic alcohol and organic solvent, if employed, is in the range from about 1 to about 35 minutes, and preferably from about 3 to about 15 minutes.

The molar ratio of organic alcohol to sodium hypochlorite in the liquid is in the range from about 1:1 to about 10:1, and preferably from about 2:1 to about 5:1.

Any organic alcohol capable of being chemically transformed into the corresponding organic hypohalite may be utilized in the process of this invention. It has been found convenient to employ those organic alcohols which are liquid at the processing temperatures herein described.

To simplify the description, the invention will be defined in terms of organic alcohol, but one skilled in the art will recognize that the term "organic alcohol" also includes mixtures of organic alcohols.

As used throughout the description and claims, the term "alkyl" is intended to include straight chain, cyclic, substituted straight chain and substituted cyclic alkyl groups. As used throughout the description and claims, the term "aryl" is intended to include normal and substituted aromatic groups.

Other alcohols which may be used in the process of this invention are cyclohexanol and related cyclic alcohols.

Other organic alcohols employed may be tertiary diols of the formula,

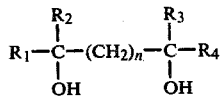

where n is an integer from 1 to about 10 and $R_1$, $R_2$, $R_3$, and $R_4$ are each selected from a group consisting of alkyl and aryl groups having 1 to about 10 carbon atoms each. Tertiary diols of this type are 2,5-dimethyl-2,5-hexanediol, 2,4-dimethyl-2,4-pentanediol, 2,4-dimethyl-2,4-hexanediol, and 2-methyl-4-ethyl-2,4-hexanediol.

Other examples of organic alcohols which may be used in this process are tertiary alcohols of the formula,

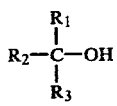

where $R_1$, $R_2$, and $R_3$ are each selected from a group consisting of alkyl and aryl groups having 1 to about 10 carbon atoms each. Tertiary alcohols of this type are 2-methyl-2-propanol (tertiary butyl alcohol), 2-methyl-2-butanol (tertiary amyl alcohol), 3-methyl-3-pentanol, 2-methyl-2-pentanol, 3-ethyl-3-pentanol, 3-isopropyl-3-pentanol, 2,3-dimethyl-3-pentanol, 2,3-dimethyl-2-pentanol, 3-ethyl-3-octanol, 5-butyl-5-nonanol, 2,7-dimethyl-3-octanol, 2-methyl-2-octanol, 4-ethyl-4-heptanol, 2-methyl-2-heptanol, 3-methyl-3-heptanol, 4-methyl-4-heptanol, 4-propyl-4-heptnol, 3-ethyl-3-hexanol, 3-ethyl-5-methyl-3-hexanol, 2-methyl-2-hexanol, 3-hexanol, 2,3,5-trimethyl-2-hexanol, 2,3,4-trimethyl-2-hexanol, 2,2,3-trimethyl-3-hexanol, 2,3,5-trimethyl-3-hexanol, 3,4,4-trimethyl-3-hexanol, 3,5,5-trimethyl-3-hexanol, 2,4-dimethyl-2-pentanol, 3-ethyl-2-methyl-3-pentanol, 2-phenyl-2-pentanol, 3-phenyl-3-pentanol, 2,4,4-trimethyl-2-pentanol, 2,3-dimethyl-2-butanol, 2,3,3-trimethyl-2-butanol, and triphenylmethanol.

The organic solvent, if employed, may be admixed with the liquid and organic alcohol before or after admixing the organic alcohol with the liquid.

The organic solvent used in this invention may be an essentially inert liquid essentially immiscible with water. The organic solvent extracts from the solution organic hypochlorites and significant quantities of any unreacted organic alcohol, while minor amounts of unreacted organic alcohol and organic hypochlorite will be contained in an aqueous phase.

The proportion of solvent will vary with the nature of the solvent and the organic hypohalite, but sufficient solvent is present at all times to extract the maximum proportion of organic hypohalite from the aqueous phase.

The weight ratio of organic solvent employed to organic alcohol is in the range from about 1:1 to about 5:1, and preferably from about 1.2:1 to about 3:1.

Suitable solvents include a wide variety of halogenated hydrocarbons and organic phosphate compounds. A typical family of halogenated hydrocarbon solvents are those represented by the formula $CH_xCl_y$ where $x+y=4$ and y is an integer from 2 to 4.

Examples of suitable members of this family of solvents include $CCl_4$, $CHCl_3$, and $CH_2Cl_2$.

Another example of a suitable family of organic solvents is of the formula $C_2H_xF_y$ where y is an integer from 1 to 2 and $x+y=6$. Examples are 1,2-difluoroethane, 1,1-difluoroethane, and fluoroethane, Another example of a suitable family of organic solvents is of the formula $C_3H_xCl_y$ where y is an integer from 1 to about 4 and $x+y=8$.

Examples of this family include isopropyl chloride, 1,2-dichloropropane, 1,1,1,2-tetrachloropropane, and 1,1,2,2-tetrachloropropane.

Another example of a suitable family of organic solvents is a tertiary halide of the formula

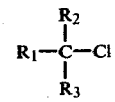

where $R_1$, $R_2$, and $R_3$ are each selected from a group consisting of alkyl and aryl groups having from 1 to about 10 carbon atoms each. Solvents include 2-chloro-2-methylpropane, 2-chloro-2-methylbutane, 2-chloro-2-methylpentane, and 3-chloro-3-ethylpentane.

Other examples of suitable organic solvents include 2-chlorotoluene, 3-chlorotoluene, 4-chlorotoluene, and alpha-chlorotoluene.

Other solvents which may be used include chlorobenzene, 1,2-dichlorobenzene, 1,3-dichlorobenzene, 1,2,4-trichlorobenzene, and fluorobenzene.

Another example of suitable organic solvents is of the formula

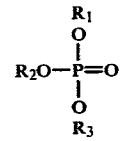

where $R_1$, $R_2$, and $R_3$ are each selected from a group consisting of alkyl and aryl groups, for example, methyl, ethyl, n-butyl, isopropyl, n-pentyl, isobutyl, n-propyl, phenyl, 2-tolyl, 3-tolyl, or 4-tolyl. In general, each alkyl or aryl group has 1 to about 10 carbon atoms. Organic phosphates of this type are tri-methyl phosphate, tri-ethyl phosphate, tri-n-butyl phosphate, tri-n-propyl phosphate, tri-isopropyl phosphate, tri-n-pentyl phosphate, tri-isobutyl phosphate, tri-phenyl phosphate, tri-2-tolyl phosphate, tri-3-tolyl phosphate, and tri-4-tolyl phosphate.

Another example of a suitable organic solvent family is of the formula $C_2F_xCl_y$ where y is an integer from 2 to 6 and $x+y=6$.

Examples of this family include 1,1,1-trichloro-2,2,2-trifluoroethane, 1,1-dichloro-1,2,2,2-tetrafluoroethane, hexachloroethane, fluoropentachloroethane, and 1,1,2-trichloro-1,2,2-trifluoroethane.

Another example of a suitable family of organic solvents is of the formula $$C_2H_xCl_y$$

where y is an integer from 1 to 6 and x+y=6.

Examples of this family include 1,2-dichloroethane, 1,1,1-trichloroethane, 1,1,2-trichloroethane, 1,1,1,2-tetrachloroethane, 1,1,2,2-tetrachloroethane, and pentachloroethane.

To simplify the description, the invention defined in terms of "organic solvent", but one skilled in the art will recognize that the term "organic solvent" also includes mixtures of organic solvents.

In a second reaction step, a halogenating agent such as chlorine is added to the organic-aqueous solution and reacts with sodium hypochlorite and an organic alcohol such as tertiary butyl alcohol, in the organic-aqueous solution to form tertiary butyl hypochlorite, sodium chloride, and water according to the equation (6):

$$NaOCl + Cl_2 + 2(CH_3)_3COH \rightarrow 2(CH_3)_3COCl + NaCl + H_2O. \qquad (6)$$

The molar ratio of chlorine to sodium hypochlorite in the liquid from the first reaction step is in the range from about 1:1 to about 10:1, and preferably from about 1.5:1 to about 5:1.

The temperature of the second reaction step is in the range from about 15° C. to about 50° C., and preferably from about 25° C. to about 40° C.

The time required for the completion of equation (6) is in the range from about 5 to about 180 minutes, and preferably from about 15 to about 120 minutes.

Completion of the reaction represented in equation (6) results in the formation of a mixture of an aqueous phase and an organic phase, the organic phase having an organic hypohalite such as tertiary butyl hypochlorite, dissolved therein.

The mixture is conveyed to a phase separator, when the mixture is separated into aqueous and organic phases.

The aqueous phase containing sodium chloride, with small amounts of sodium chlorate, sodium hydroxide, and sodium hypochlorite may be used as a reactant in a chlor-alkali electrolytic cell, or may be sent to waste treatment as effluent.

The organic phase containing organic hypochlorite, organic alcohol, and organic solvent may be used as a chlorinating agent or may be treated with an acid, such as hydrochloric acid, to reclaim free chlorine.

The difference between the density of the organic phase which contains organic solvent, organic alcohol, and organic hypochlorite, and the density of the aqueous phase which contains organic alcohol, sodium chloride, sodium chlorate, and sodium hydroxide is preferably of at least sufficient magnitude so that physical phase separation can be practiced by methods recognized by those skilled in the art. Large density differences facilitate easy separation of the organic phase from the aqueous phase by conventional phase separation techniques.

The process of this invention produces an aqueous alkali metal halide solution which may be utilized as brine feed to an electrolytic cell with appropriate purification. In addition, an organic hypohalite is formed which is recycled to the basic calcium hypochlorite process as a chlorinating agent.

By treating waste streams produced in calcium hypochlorite plants, the process of this invention minimizes the amount of material required to be discharged to and processed in waste treatment plants.

The following example is presented to define the invention more fully without any intention of being limited. All parts and percentages are by weight unless otherwise specified.

EXAMPLE 1

About 198 parts of a solution which analyzed

| Component | Percent |
|---|---|
| $Ca(OCl)_2$ | 9.6 |
| $CaCl_2$ | 0.98 |
| NaCl | 18.16 |
| $H_2O$ | remainder, | was admixed with about 26 parts of an aqueous solution of about 50% sodium hydroxide. The mixture was stirred for about 15 minutes and filtered at atmospheric pressure through a glass pad filter for about three hours.

About 158 parts of the resulting filtrate which analyzed

| Component | Percent |
|---|---|
| NaOCl | 8.5 |
| NaOH | 0.8 |
| $CaCl_2$ | 0 |
| NaCl | 16.0 |
| $H_2O$ | remainder | were admixed with about 21 parts tertiary butyl alcohol and about 230 parts of 1,1,2-trichloro-1,2,2-trifluoroethane in a glass flask. Molecular chlorine gas was bubbled through the solution for about 15 minutes at a temperature of about 25° C. An organic phase (about 248 parts) and an aqueous phase (about 150 parts) were formed. The organic phase, after separation from the aqueous phase, was analyzed and found to contain 18.5 parts of tertiary butyl hypochlorite.

The percent conversion of sodium hypochlorite, defined as 100 times (the ratio of chemical equivalents of sodium hypochlorite used divided by the chemical equivalents of sodium hypochlorite originally present), was about 46%.

The percent yield of tertiary butyl hypochlorite, defined as 100 times (the ratio of chemical equivalents of teritary butyl hypochlorite formed divided by the chemical equivalents of sodium hypochlorite used), was about 47%.

What is claimed is:

1. A process for recovering recoverable chlorine as organic hypohalite and an alkali metal halide from an impure aqueous solution containing alkaline earth metal halide, alkaline earth metal hypohalite and alkaline earth metal chlorate which comprises:
   (a) reacting said impure aqueous solution with alkali metal hydroxide to form a slurry of solid particles of alkaline earth metal hydroxide suspended in a liquid, wherein the molar ratio of said alkali metal hydroxide to total moles of alkaline earth metal species is in the range from about 1.5:1 to about 3:1 to complete conversion of all the alkaline earth metal species,
   (b) separating said alkaline earth metal hydroxide from said liquid, (c) admixing said liquid with an organic alcohol to form an organic-aqueous solution, wherein said alcohol is selected from a group consisting of tertiary alcohols, cyclic alcohols, and mixtures thereof, (d) reacting a halogenating agent with said organic-aqueous solution to form an aqueous phase and an organic phase, said organic phase having an organic hypohalite dissolved therein, and (e) separating said aqueous phase from said organic phase.

2. The process of claim 1, wherein said alkaline earth metal halide is calcium halide.

3. The process of claim 2, wherein said calcium halide is calcium chloride.

4. The process of claim 3, wherein said alkaline earth metal hypohalite is calcium hypohalite.

5. The process of claim 4, wherein said calcium hypohalite is calcium hypochlorite.

6. The process of claim 5, wherein said alkali metal hydroxide is sodium hydroxide.

7. The process of claim 6, wherein said halogenating agent is chlorine.

8. The process of claim 1, wherein an organic solvent is admixed with said liquid and said organic alcohol.

9. The process of claim 2, wherein the temperature of the process is in the range from about 20° C. to about 50° C.

10. The process of claim 9, wherein the temperature of the process is in the range from about 25° C. to about 40° C.

11. The process of claim 10, wherein the molar ratio of sodium hydroxide to total calcium species of said impure aqueous stream is in the range from about 2:1 to about 2.5:1.

12. The process of claim 11, wherein the molar ratio of said organic alcohol to said sodium hypochlorite is in the range from about 1:1 to about 10:1.

13. The process of claim 12, wherein the molar ratio of said organic alcohol to said sodium hypochlorite is in the range from about 2:1 to about 5:1.

14. The process of claim 13, wherein the molar ratio of said chlorine to said sodium hypochlorite is in the range from about 1:1 to about 10:1.

15. The process of claim 14, wherein the molar ratio of said chlorine to said sodium hypochlorite is in the range from about 1.5:1 to about 5:1.

16. The process of claim 1, wherein said organic alcohol is a tertiary alcohol of the formula,

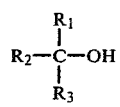

where $R_1$, $R_2$, and $R_3$ are each selected from a group consisting of alkyl and aryl groups having 1 to about 10 carbon atoms each.

17. The process of claim 16, wherein said organic alcohol is tertiary butyl alcohol.

18. The process of claim 16, wherein said organic alcohol is tertiary amyl alcohol.

19. The process of claim 16, wherein said organic alcohol is 3-methyl-3-pentanol.

20. The process of claim 1 wherein said organic alcohol is a tertiary diol of the formula,

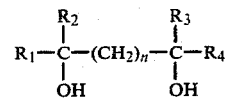

where n is an integer from 1 to about 10 and $R_1$, $R_2$, $R_3$, and $R_4$ are each selected from a group consisting of alkyl and aryl groups having 1 to about 10 carbon atoms each.

21. The process of claim 1, wherein said organic alcohol is cyclohexanol.

22. The process of claim 1, wherein an essentially inert organic solvent essentially immiscible with water is admixed with said organic alcohol.

23. The process of claim 22, wherein said organic solvent is of the formula, $$CH_xCl_y$$

where $x+y=4$ and y is an integer from 2 to 4.

24. The process of claim 22, wherein said organic solvent is an organic phosphate of the formula,

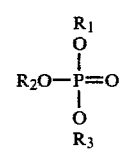

where $R_1$, $R_2$, and $R_3$ are each selected from a group consisting of alkyl and aryl groups having 1 to about 10 carbon atoms each.

25. The process of claim 22, wherein said organic solvent is of the formula, $$C_2F_xCl_y$$

where y is an integer from 2 to 6 and $x+y=6$.

26. The process of claim 22, wherein said organic solvent is of the formula, $$C_2H_xCl_y$$

where y is an integer from 1 to 6 and $x+y=6$.

27. The process of claim 22, wherein said organic solvent is of the formula, $$C_2H_xF_y$$

where y is an integer from 1 to 2 and $x+y=6$.

28. The process of claim 22, wherein said organic solvent is of the formula, $$C_3H_xCl_y$$

where y is an integer from 1 to about 4 and $x+y=8$.

29. The process of claim 22, wherein said organic solvent is a tertiary halide of the formula,

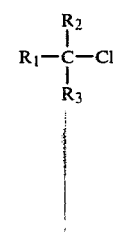

where $R_1$, $R_2$, and $R_3$ are each selected from a group consisting of alkyl and aryl groups having from 1 to about 10 carbon atoms each.

30. The process of claim 23, wherein said organic solvent is $CCl_4$.

31. The process of claim 22, wherein said organic solvent is selected from a group consisting of 2-chlorotoluene, 3-chlorotoluene, 4-chlorotoluene, and alpha-chlorotoluene.

32. The process of claim 22, wherein said organic solvent is selected from the group consisting of chlorobenzene, 1,2-dichlorobenzene, 1,3-dichlorobenzene, 1,2,4-trichlorobenzene, and fluorobenzene.

33. The process of claim 22, wherein said organic solvent is 1,1,2-trichloro-1,2,2-trifluoroethane.

34. The process of claims 7, 8, 15, or 17 wherein tertiary butyl chloride is admixed with said organic alcohol.

* * * * *